United States Patent
Meza Almendra et al.

(10) Patent No.: US 10,190,074 B1
(45) Date of Patent: Jan. 29, 2019

(54) COMPOSITION COMPRISING CHOLESTEROL

(71) Applicant: Golden Omega S.A., Las Condes, Santiago (CL)

(72) Inventors: Julio César Meza Almendra, Arica (CL); José Luis Lopez Castillo, Arica (CL); Pablo Napolitano Feito, Arica (CL); Gustavo Adolfo Dorlhiac Silva, Arica (CL); Luis Tomás Pincheira Varas, Arica (CL); Alejandro Markovits Rojas, Arica (CL)

(73) Assignee: GOLDEN OMEGA S.A., Las Condes (CL)

( * ) Notice: Subject to any disclaimer, the term of this patent is extended or adjusted under 35 U.S.C. 154(b) by 0 days.

(21) Appl. No.: 15/896,132

(22) Filed: Feb. 14, 2018

(51) Int. Cl.
| | |
|---|---|
| *C11B 1/10* | (2006.01) |
| *C11B 1/12* | (2006.01) |
| *C07J 9/00* | (2006.01) |
| *B01D 3/10* | (2006.01) |
| *C11B 3/12* | (2006.01) |

(52) U.S. Cl.
CPC ............... *C11B 1/10* (2013.01); *B01D 3/10* (2013.01); *C07J 9/00* (2013.01); *C11B 3/12* (2013.01); *B01D 2257/70* (2013.01)

(58) Field of Classification Search
CPC ........................................................ C07J 9/00
See application file for complete search history.

(56) References Cited

U.S. PATENT DOCUMENTS

| | | | | |
|---|---|---|---|---|
| 6,136,368 | A | 10/2000 | Fitie | |
| 7,678,930 | B2 * | 3/2010 | Sondbo | ............... A23D 9/00 554/12 |
| 7,718,698 | B2 * | 5/2010 | Breivik | ............... A23D 9/00 514/558 |

FOREIGN PATENT DOCUMENTS

GB 489623 A 7/1938

OTHER PUBLICATIONS

Suseno et al, Oriental Journal of Chemistry, Optimization of Sardine Oil Neutralization Process from Fish Meal Industry by-product, 2015, 31(4), pp. 2507-2514. (Year: 2015).*

* cited by examiner

*Primary Examiner* — Paul A Zucker
(74) *Attorney, Agent, or Firm* — Blank Rome LLP

(57) ABSTRACT

Disclosed is a process for producing a cholesterol concentrate including the steps of (a) distilling a fish oil having no more than 2% free fatty acids in an admixture with an auxiliary fluid in a vacuum distillation column to obtain a first distillate and a first residue; and (b) distilling the first distillate in a vacuum distillation column to obtain a second distillate and a second residue, wherein the second residue includes the cholesterol concentrate.

17 Claims, No Drawings

COMPOSITION COMPRISING CHOLESTEROL

FIELD OF THE INVENTION

The present invention is related to a process for the production from fish oil having a low free fatty acid content, a composition comprising cholesterol and its use in animal feed, especially in shrimp and prawn feed.

BACKGROUND

Cholesterol in Animal Feed Formulation

Formulated Feed for Shrimp and Prawn Mass Culture and Feed Ingredients.

Formulated feed for shrimp and prawn mass culture is a very complex mixture of numerous ingredients from different sources specifically addressed to supply the nutrients and energy shrimp and prawn need for best growth. (FAO: www.fao.org/fishery). A complete feed is a formulated pellet that provides all required nutrients in the proper proportions necessary for rapid weight gain, high feed efficiency and necessary for shrimp and prawn health and quality.

Cholesterol, and the fatty acids eicosapentaenoic acid (EPA), docosahexaenoic acid (DHA), linoleic acid (LA), and alpha-linolenic acid (ALA) are among the several essential nutrients which cannot be synthesized by shrimp or prawn, so a dietary source is essential.

Typically, fish oils incorporated into the formulated pellet at 2 to 3 percent, provide the essential fatty acids EPA and DHA, meanwhile vegetable oils like soybean oil and linseed oil provide the essential fatty acids LA and ALA. Dietary requirements of EPA and DHA for shrimp and prawn range from 0.5 to 1.0 percent in the feed. The total lipid content of the formulated pellet should be in the range of 6 to 9%.

Fish oil also contains, on the average, about 1% of total (free and esterified) cholesterol but this does not suffice alone to satisfy the cholesterol requirements of shrimp or prawn, because fish oil which is included typically at 2 to 3% in the feed would contribute at most only 0.02-0.03% of cholesterol in the diet instead of 0.5 to 1.0%, which is the range of the dietary requirement of cholesterol for shrimp and prawn.

GB 489623 discloses a process for obtaining cholesterol from marine animal oils by subjecting the oil to fractionation through multiple sequential vacuum distillations at different temperature and pressure, wherein one or more of the distillate fractions comprise cholesterol, both free and esterified. Such fractions comprising cholesterol, if desired, may be further purified by methods such as saponification followed by extraction of non-saponifiable matter with a water immiscible solvent, concentration and crystallization.

An embodiment of the disclosed process is Example 1 of GB 489623, wherein clarified whale oil is subjected to molecular distillation at a temperature of 90° C.-220° C. and a pressure of about 0.001 to 0.003 mmHg. As the pressure is lowered and the temperature is raised, successive fractions amounting to 0.2 to 2% are withdrawn, such fractions comprising most of the free fatty acids, squalene and other volatiles. More fractions in proportions ranging from 0.5 to 10% are withdrawn between about 120° C. and 160° C., such fractions comprising free and esterified cholesterol. To a skilled person, it is evident that that no less than four consecutive distillations, each at some specific temperature and pressure, are required to arrive at a cholesterol rich fraction.

There are several disadvantages of the process disclosed by GB 489623. At present, fish oil is a valuable commodity due to its content of eicosapentaenoic (EPA) and docosahexaenoic (DHA) acid. Multiple distillations of fish oil increase the trans fatty acid content of the oil, and promote polymerization of unsaturated fatty acid, which in turn decreases the content of EPA and DHA. Multiple distillations also render the fish oil unsuitable for human or animal consumption.

On the other hand, present day fish oils contain a great variety of toxic and/or harmful anthropogenic contaminants like polychlorinated biphenyls (PCB), dichlorodiphenyltrichloroethane (DDT) and its metabolites, dibenzo-dioxins (PCDDs), and dibenzo-furans (PCDFs), poly-aromatic hydrocarbons (PAH), pesticides and their degradation products, also known as persistent organic pollutants or POP's, which are resistant to environmental degradation and thus bio-accumulate. Therefore, the distillate fractions comprising cholesterol will comprise as well one or more of such contaminants. The content of such contaminants in the distillate fractions will be even higher than in the fish oil. This fact, though evident, can be found in the prior art.

U.S. Pat. No. 7,678,930 discloses a process for obtaining a free cholesterol-reduced fish oil by vacuum stripping the oil. On the other hand, U.S. Pat. No. 7,718,698 discloses a process for decreasing the amount of environmental pollutants in fish oil, also by vacuum stripping the oil. These two patents have similar disclosures. Therefore, under conditions of vacuum distillation where environmental pollutants are removed, free cholesterol is removed as well and vice versa.

The distillate of the process of U.S. Pat. No. 7,678,930 has a level of toxic and/or harmful anthropogenic contaminants higher than the fish oil and its cholesterol content is no greater than 10%, therefore it is unsuitable as a source of cholesterol in formulated shrimp and prawn feed. The same can be said of the cholesterol concentrates obtained by the process disclosed in GB 489623, which is an additional disadvantage of such process.

U.S. Pat. No. 6,136,368 discloses the use of the residue or pitch in the distillation of crude fatty acids of animal origin obtained upon hydrolysis of fat of cattle, pigs, poultry, sheep or fish oil. The process would increase the cholesterol content up to 20 times the original cholesterol content. Although the process leads to a cholesterol containing ingredient less expensive than the high purity cholesterol currently utilized in the feed of farmed crustaceans, i.e. the 90% or more pure cholesterol produced from lanolin or sheep wool grease, it has several disadvantages. For example, in case fish oil was utilized, its hydrolysis leads to the splitting of the fish oil triglycerides, a valuable commodity by itself in the commercially less valuable free fatty acids and glycerol.

Concerning the pitch or residue of the distillation containing cholesterol, claimed in U.S. Pat. No. 6,136,368 as feed ingredient to feed crustaceans, it is questionable whether it could be useful for such purpose. In column 2, lines 60-65 of the patent it is said: "This residue 21 is called "pitch" and contains many sterols that have a higher boiling point than fatty acids and are part of the reason why the residue cannot be distilled. The pitch contains a number of substances that are not clearly defined, such as free fatty acids, polymerized fatty acids, sterols (vitamin E, cholesterol and other sterols), impurities, etc. The polymerized fatty acids and impurities give the pitch its typical black colour."

A cholesterol containing ingredient, also containing polymerized fatty acids (presumably mostly polymerized polyunsaturated fatty acids) and a "number of substances that are not clearly defined" does not seem to be a good alternative to the cholesterol the shrimp and prawn farmers are currently using.

Currently the main commercial source of cholesterol used in the cultivation of crustaceans like shrimps and prawns is the non-saponifiable or alcoholic fraction of lanolin or wool wax comprising from about 25% to about 32% of cholesterol. However, such fraction cannot be utilized directly as feed ingredient in aquaculture because it contains a great variety of other sterols and uncommon fatty acids not found in marine or aquatic species, which constitute anti-nutritional factors (ANFs). In order to be utilized as feed additive, the cholesterol content of the alcoholic fraction of lanolin has to be increased to at least 90% in order to reduce or remove most such ANFs. The purification process of cholesterol from lanolin requires several process steps of high chemical demand (precipitation) and solvents (crystallization), yielding to high energy consumption for solvent recovery and environmental impact. This makes cholesterol the most expensive single ingredient for use in shrimp and prawn feeds. Its substitution by less expensive cholesterol like the cholesterol containing composition of the present invention would greatly contribute to the reduction of the feed cost which is currently about half of variable production costs in shrimp and prawn culture.

It is therefore an objective of the present invention to provide a process for obtaining from fish oil having a low free fatty acid content, a composition comprising at least 20% of cholesterol and the use of the composition in animal feed, especially in shrimp and prawn feed. The disclosed process thus produces a residual or processed fish oil of high-quality suitable for animal or human consumption or for the elaboration of EPA and DHA concentrates.

SUMMARY OF THE INVENTION

In one aspect, the disclosed technology relates to a process for producing a composition comprising cholesterol, comprising the steps of: (a) distilling a fish oil comprising at most 2% free fatty acids in an admixture with an auxiliary fluid in a vacuum distillation column to obtain a first distillate and a first residue and, (b) distilling the first distillate in a vacuum distillation column to obtain a second distillate and a second residue, wherein the second residue comprises the composition comprising cholesterol.

In one embodiment, the weight ratio of the auxiliary fluid to the fish oil in the admixture is about 1:100 to 10:100. In another embodiment, the vacuum distillation column is a short-path distillation column. In another embodiment, the admixture is fed into the vacuum distillation column in step (a) at a rate of 1 to 150 kg/h per $m^2$ of evaporator area. In another embodiment, step (a) is conducted at a distillation temperature of 150 to 300° C. and a column pressure of 0.0001 to 0.5 mbar. In another embodiment, the distillation temperature in step (a) is 180 to 280° C. and the column pressure is 0.001 to 0.1 mbar. In another embodiment, the first distillate is fed into the vacuum distillation column in step (b) at a rate of 10 to 350 kg/h per $m^2$ of evaporator area. In another embodiment, step (b) is conducted at a distillation temperature of 100 to 250° C. and a column pressure of 0.0001 to 0.5 mbar. In another embodiment, the composition comprising cholesterol comprises at least 20% cholesterol.

In another embodiment, the composition comprising cholesterol has a lower content of anthropogenic contaminants than the fish oil.

DETAILED DESCRIPTION OF THE INVENTION

Fish oil contains, on the average, about 1% of total (free and esterified) cholesterol but this does not suffice alone to satisfy the cholesterol requirements of the shrimp or prawn, because as mentioned above, fish oil is included typically at 2 to 3% in the feed, and would thus contribute at most 0.02-0.03% of cholesterol only, instead of the 0.5 to 1.0% range for the dietary requirements of cholesterol for shrimp and prawn.

As used here, the term "fish oil" refers to oils obtained from wild and farmed fish, crustaceans and other marine animals. Such oils are obtained from the whole body of the fish or from its by-products such as liver, head etc. Examples of such oils comprise anchovy oil, sardine oil, salmon oil, jack mackerel oil, menhaden oil, tuna oil, krill oil, squid oil, pollock oil, herring oil, capelin oil, cod liver oil and squid oil. Fish oils may be derived from a single species or mixtures of fish oils.

Fish oil also refers to any fish oil from fish oil/meal factories, including degummed or bleached fish oil. Such oils, in addition to triglycerides, their main component, typically comprise between 1 to 10% of free fatty acids and about 2% or less of non-saponifiable matter composed primarily of cholesterol, glyceryl ethers, fatty alcohols, squalene and saturated hydrocarbons. (Young, F.V.K. "The Chemical & Physical Properties of Crude Fish Oils for Refiners & Hydrogenators" Fish Oil Bulletin No. 18, 1986). The average cholesterol content of fish oil is about 1%.

In addition, conventional fish oils contain a great variety of toxic and/or harmful anthropogenic contaminants like polychlorinated biphenyls (PCB), DDT and its metabolites, dibenzo-dioxins (PCDDs), and dibenzo-furans (PCDFs), poly-aromatic hydrocarbons (PAH), pesticides and their degradation products, also known as persistent organic pollutants or POP's, which are resistant to environmental degradation and thus bio-accumulate.

It is a surprising feature of the present invention that the cholesterol containing compositions obtained according to the process described below have a lower content of anthropogenic contaminants than the fish oils these compositions are obtained from.

In the present invention a fish oil having low content of free fatty acids means a fish oil comprising at most 2% of free fatty acids. Such fish oil might come directly from a fish oil/meal factory or might correspond to a neutralized fish oil.

Neutralized fish oil is a fish oil that has been processed through an alkali refining or neutralization step to reduce its free fatty acid content (FFA) to an acid value less than 2 mg KOH/g. Commonly referred to as neutralization, an alkali, e.g., NaOH or KOH, is added to the fish oil in a reactor and heated to react with the free fatty acids to form soaps, which are then centrifuged out. Washing with water completes the neutralization of the oil. Typically, fish oil is first subjected to a degumming step with phosphoric acid to reduce its phospholipids content, and then is neutralized with caustic soda to reduce its FFA content.

In the present invention a vacuum distillation column may be a short-path distillation column having an internal condenser at the proximity of the heated surface or evaporator. The short-path distillation column is also known as a molecular distillation column when the distance between the evaporator and the condenser is comparable to the mean free path of the distillate molecules under the operating conditions. Therefore, in the present invention a vacuum distillation column may be a short-path distillation column, a molecular distillation column, or an equivalent thereof.

a) Distilling the Admixture of Auxiliary Fluid with Fish Oil Having Low Content of Free Fatty Acids.

Cholesterol having a melting point of 136° C. at the temperature of the condenser, which is preferably lower than 60° C., may form a very viscous slow flowing film at the condenser or may even solidify, thus clogging the condenser.

An auxiliary fluid (AF) includes any fluid or mixture of fluids which distills at the vacuum distilling conditions disclosed below, and is also in a liquid state at the condenser temperature and dissolves or is miscible with cholesterol, thus reducing its concentration in the condensed film, therefore forming a free downward flowing fluid mixture at the condenser, and preventing clogging or fouling of the condenser. Any fluid or fluid mixture fulfilling the above requirements can be used as an auxiliary fluid, though preferred auxiliary fluids for the present invention include ethyl esters of unsaturated fatty acids or mixtures of ethyl esters of fatty acids mostly composed of unsaturated fatty acids, because such auxiliary fluids allow the use of lower condenser temperatures, which in turn improves the vacuum system performance and reduces the re-evaporation rate of the condensates, thereby improving the overall removal yield of the desired distillate.

The admixture in an auxiliary fluid free basis is fed into the vacuum distillation column, generally at a rate from 1 to 150 kg/h per $m^2$ of evaporating surface, preferably from 10 to 100 kg/h per $m^2$.

The proportion of auxiliary fluid relative to the fish oil having low content of free fatty acids can be from 1 to 10%, preferably from 2 to 8%.

In an embodiment, the evaporation temperature is between 150° C. and 300° C., preferably between 180° C. and 280° C. In an embodiment, the column pressure is between 0.0001 mbar and 0.5 mbar, preferably between 0.001 and 0.1 mbar. In an embodiment, the evaporation temperature is between 150° C. and 300° C., preferably between 180° C. and 280° C. and the column pressure is between 0.0001 mbar and 0.5 mbar, preferably between 0.001 and 0.1 mbar.

The distillation process results in the separation of a first distillate comprising cholesterol, other non-saponifiable matter of the fish oil and anthropogenic contaminants, and a first residue comprising fish oil with decreased content of cholesterol, non-saponifiable matter and anthropogenic contaminants. The first distillate condenses at the internal condenser. The first distillate and the first residue leave the column separately and are collected at the column exit. The first residue is a high quality fish oil suitable for human an animal consumption or for the elaboration of EPA and DHA concentrates.

b) Distilling the First Distillate

The first distillate is fed into a vacuum distillation column at a rate from 10 to 350 kg/h per $m^2$ of evaporating surface, preferably from 50 to 200 kg/h per $m^2$.

In an embodiment, the evaporation temperature is between 100° C. and 250° C., preferably between 140° C. and 220° C. In an embodiment, the column pressure is between 0.0001 mbar and 0.5 mbar, preferably between 0.001 and 0.1 mbar. In an embodiment the evaporation temperature is between 100° C. and 250° C., preferably between 140° C. and 220° C., the column pressure is between 0.0001 mbar and 0.5 mbar, preferably between 0.001 and 0.1 mbar.

The distillation process of the first distillate results in the production of a second distillate which condenses at the internal condenser, and a second residue comprising cholesterol and a content of anthropogenic contaminants, such as POPs and heavy metals, that is less than the fish oil.

The second distillate and the second residue leave the vacuum distillation column separately and are collected at the column exit.

The second residue is a composition comprising at least 20% of cholesterol and can be used as a cholesterol-containing ingredient for shrimp and prawn feed.

A better understanding of the present invention may be obtained in light of the following examples which are set forth to illustrate, but are not to be construed to limit the present invention.

Comparative Example

Cholesterol Concentrates from Anchovy Oil According to the Process of Patent GB 489623.

Anchovy oil was processed according the to process disclosed in patent GB 489623, as embodied in Example 1 of GB 489623 for whale oil.

100 kg of the anchovy oil having a total cholesterol content of 7.4 mg/g was fed to a VK 83 short path distillation column and distilled at the temperature of 90° C. and the pressure of 0.003 mbar. The condenser temperature was set at 50° C. A distillate D1 in the amount of 1.6 kg was obtained together with a residue R1, the residual anchovy oil of the first distillation. The content of cholesterol of D1 was below 0.1%.

Next, R1 was fed to a VK 83 short path distillation column and distilled at the temperature of 130° C. and the pressure of 0.002 mbar. The condenser temperature was set at 50° C. A distillate D2 in the amount of 1.1 kg was obtained together with a residue R2, the residual anchovy oil of the second distillation. The content of cholesterol of D2 was 0.8%.

As the D2 split was low, around 1%, the following distillations were done using an auxiliary fluid of the composition shown in Table 1 below. It should be noted, that in similar circumstances, use of an auxiliary fluid may help prevent the clogging of the condenser, as disclosed in U.S. Pat. No. 2,126,467.

R2 was admixed with 5 kg of auxiliary fluid of the composition shown in Table 1 and the mixture was fed to a VK 83 short path distillation column and distilled at the temperature of 180° C. and the pressure of 0.002 mbar. The condenser temperature was set to 20° C. A distillate D3 in the amount of 5.8 kg was obtained together with a residue R3, the residual anchovy oil of the third distillation. The content of cholesterol in D3 was 6.6%.

Next, R3 was admixed with 5 kg of auxiliary fluid of the composition shown in Table 1 and the mixture was fed to a VK 83 short path distillation column and distilled at the temperature of 220° C. and the pressure of 0.002 mbar. The condenser temperature was set to 20° C. A distillate D4 in the amount of 5.3 kg was obtained together with a residue R4, the residual anchovy oil of the third distillation. The content of cholesterol in D4 was 6.2%.

TABLE 1

Auxiliary fluid composition in Comparative Example.

| Fatty acid ethyl ester | Composition concentration, % |
|---|---|
| Myristic acid (C14:0) ethyl ester. | 6.6 |
| Palmitic acid (C16:0) ethyl ester | 8.2 |
| Palmitoleic acid (C16:1) ethyl ester | 46.4 |
| Stearic acid (C18:0) ethyl ester | 1.9 |
| Oleic acid (C18:1) ethyl ester | 29.3 |
| Linoleic acid (C18:2) ethyl ester | 4.1 |
| Alpha-linolenic acid (18:3) ethyl ester | 3.5 |

The total amount of cholesterol in the combined distillate fractions D2, D3 and D4 is 720.2 g, which is tantamount to a cholesterol recovery yield of 97.3%. However, the concentration of cholesterol in the combined distillate fractions is only 5.9%, therefore to provide 1% of cholesterol in the shrimp and prawn feed, 17 g of the combined distillate fractions is needed (per 100 g of feed), which rules out its use for such purpose, without further processing to achieve a cholesterol content of at least 20%.

In addition, the total poly aromatic hydrocarbons (PAH) in the combined distillate fractions amounted to 88.5 ppb, which is higher than in the original anchovy oil.

Concerning the residual fish oil of each distillation, Table 2 shows the combined EPA and DHA content, trans fatty acid content and acid number of each residue.

TABLE 2

Combined EPA and DHA content, trans fatty acid content and acid number

| | Anchovy Oil | R1 | R2 | R3 | R4 |
|---|---|---|---|---|---|
| EPA + DHA, % | 26.7 | 26.8 | 26.2 | 25.1 | 24.3 |
| Trans Fatty Acids, % | 0.3% | 0.3% | 0.4% | 0.6% | 0.7% |
| Acid Number, mg KOH/g | 6.3 | 0.3 | 0.1 | <0.05 | <0.05 |

As can be observed in Table 2, the obtaining of cholesterol fractions by fractionation of the fish oil as disclosed in patent GB 489962, leads to an increase of the trans fatty content and a loss of (EPA+DHA), presumably due to polymerization in the residual fish oil. After four successive distillations, the trans fatty acid content increased by about 130% and the EPA+DHA content decreased by about 9%.

Example 1

Cholesterol Concentrate from Neutralized Anchovy Oil

Anchovy oil (same as used in Comparative Example) was neutralized with caustic soda and washed with hot water to yield to a neutralized anchovy oil with an acid number of 0.2 mg KOH/g.

250 kg of the neutralized anchovy oil was admixed with 15 kg of auxiliary fluid of the composition shown in Table 1.

The admixture was fed to a VK 83 short path distillation column and distilled at the temperature of 253° C. and the pressure of 0.008 mbar. The condenser temperature was set at 20° C. A distillate D1 in the amount of 18 kg was obtained together with a residue R1, the residual anchovy oil of the distillation.

Next, 15 kg of distillate D1 was fed to a VK 83 short path distillation column at the temperature of 155° C. and the pressure of 0.007 mbar. The condenser temperature was set to 20° C. A residue R2 in the amount of 3.5 kg was obtained. Table 3 below presents the analytical results for Example 1.

TABLE 3

Analytical results for the Example 1.

| | Neutralized Anchovy oil | Distillate D1 | Residue R2 |
|---|---|---|---|
| Free cholesterol, mg/g | 7.0 | 92.7 | 311.2 |
| Total cholesterol, mg/g | 7.4 | 93.0 | 325.4 |
| Cholesterol ester[1], mg/g | 0.8 | 0.5 | 23.9 |
| Non-saponifiable matter, % | 1.38 | 13.40 | 33.12 |
| Acid number, mg KOH/g | 0.2 | 2.6 | 10.2 |
| Dioxins, Furans and Dioxin like PCBs, TEQ ppt (lower bound) | 1.41 | 12.83 | 0.21 |
| PCB 209, ppb (lower bound) | 18.53 | 225.27 | 2.95 |
| Total PAHs, ppb | 14.11 | 133.6 | 0.7 |
| Pesticides, ppb | 18.4 | 241.3 | <LOQ |

[1]As mg of cholesteryl oleate/g of sample; LOQ: Limit of Quantification

As can be observed, a formulated pellet comprising at most 3% of residue R2, a product of the process, is enough to meet the cholesterol requirement of shrimp and prawn. In addition, given that the total fat or lipid content in the formulated pellet for shrimps and prawns is from 6 to 9%, there remains an ample choice for additional sources of lipids, like fish and vegetable oils, to satisfy essential fatty acid requirements of the crustaceans, linoleic acid (LA), and alpha-linolenic acid (ALA), EPA and DHA.

The concentration of cholesterol in residue R2 is 32.5% and the recovery yield was 73.8%.

In addition, the cholesterol composition derived from the fish oil having a low free fatty acid content according to the process of the present invention has a lower contaminant content than the starting fish oil the composition is obtained from.

Table 4 shows the combined EPA and DHA content, trans fatty acid content and acid number of residue R1 of Example 1.

TABLE 4

Combined EPA and DHA content, trans fatty acid content and acid number of residue R1.

| | Anchovy Oil | Neutralized Anchovy Oil | R1 |
|---|---|---|---|
| EPA + DHA, % | 26.7 | 26.9 | 27.0 |
| Trans Fatty Acids, % | 0.3% | 0.3% | 0.3% |
| Acid Number, mg KOH/g | 7.1 | 0.2 | <0.05 |

Superior results are demonstrated in Example 1, contrary to the process of GB 489623 which is unable to achieve such results.

All references cited and/or discussed in this specification are incorporated herein by reference in their entireties and to the same extent as if each reference was individually incorporated by reference.

The invention claimed is:

1. A process for producing a composition comprising at least 20% by weight of cholesterol, based on 100% total weight of the composition, the process comprising the steps of:
   (a) distilling a fish oil having at most 2% by weight of free fatty acids, based on 100% total weight of the fish oil, in an admixture with an auxiliary fluid in a vacuum distillation column to obtain a first distillate and a first residue; and (b) distilling the first distillate in a vacuum distillation column to obtain a second distillate and a second residue, wherein (i) the second residue comprises the composition comprising at least 20% by weight cholesterol, based on the total weight of the composition, and (ii) the composition has a lower content of anthropogenic contaminants than the fish oil.

2. The process according to claim 1, wherein the weight ratio of the auxiliary fluid to the fish oil in the admixture is about 1:100 to 10:100.

3. The process according to claim 1, wherein the vacuum distillation column is a short-path distillation column.

4. The process according to claim 1, wherein the admixture is fed into the vacuum distillation column in step (a) at a rate, based on an auxiliary fluid free basis, of 1 to 150 kg/h per m² of evaporator area.

5. The process according to claim 1, wherein step (a) is conducted at an evaporation temperature of 150 to 300° C. and a column pressure of 0.0001 to 0.5 mbar.

6. The process according to claim 5, wherein the evaporation temperature in step (a) is 180 to 280° C. and the column pressure is 0.001 to 0.1 mbar.

7. The process according to claim 1, wherein the first distillate is fed into the vacuum distillation column in step (b) at a rate of 10 to 350 kg/h per m² of evaporator area.

8. The process according to claim 1, wherein step (b) is conducted at an evaporation temperature of 100 to 250° C. and a column pressure of 0.0001 to 0.5 mbar.

9. A process for producing a composition comprising at least 20% by weight of cholesterol, based on 100% total weight of the composition, the process comprising the steps of:
(a) distilling a fish oil having at most 2% by weight of free fatty acids, based on 100% total weight of the fish oil, in an admixture with an auxiliary fluid in a vacuum distillation column to obtain a first distillate and a first residue; and
(b) distilling the first distillate in a vacuum distillation column to obtain a second distillate and a second residue,
wherein
(i) the second residue comprises the composition comprising at least 20% by weight cholesterol, based on the total weight of the composition,
(ii) the composition has a lower content of anthropogenic contaminants than the fish oil, and
(iii) the auxiliary fluid is a fluid that distills at a temperature between about 150° C. and about 300° C. at a pressure of between about 0.0001 mbar and 5 mbar, and is miscible with cholesterol.

10. The process according to claim 9, wherein the auxiliary fluid comprises one or more ethyl esters of fatty acids.

11. The process according to claim 10, wherein the fatty acids are selected from myristic acid, palmitic acid, palmitoleic acid, stearic acid, oleic acid, linoleic acid, alpha-linolenic acid, and any combination thereof.

12. The process according to claim 10, wherein the fatty acids are unsaturated fatty acids.

13. A process for producing a composition comprising at least 20% by weight of cholesterol, based on 100% total weight of the composition, the process comprising the steps of:
(a) distilling a fish oil having at most 2% by weight of free fatty acids, based on 100% total weight of the fish oil, in an admixture with an auxiliary fluid in a vacuum distillation column to obtain a first distillate and a first residue; and
(b) distilling the first distillate in a vacuum distillation column to obtain a second distillate and a second residue,
wherein
(i) the second residue comprises the composition comprising at least 20% by weight cholesterol, based on the total weight of the composition,
(ii) the composition has a lower content of anthropogenic contaminants than the fish oil, and
(iii) the auxiliary fluid comprises one or more ethyl esters of fatty acids.

14. The process according to claim 13, wherein the fatty acids are selected from myristic acid, palmitic acid, palmitoleic acid, stearic acid, oleic acid, linoleic acid, alpha-linolenic acid, and any combination thereof.

15. The process according to claim 13, wherein the fatty acids are unsaturated fatty acids.

16. The process according to claim 13, wherein the distilling in step (b) is performed without the further addition of an auxiliary fluid.

17. The process according to claim 1, wherein step (a) is conducted at an evaporation temperature of about 180 to about 280° C. and a column pressure of about 0.001 to about 0.1 mbar.

* * * * *